(12) United States Patent
Cheng et al.

(10) Patent No.: US 7,759,533 B2
(45) Date of Patent: Jul. 20, 2010

(54) LIGHTLY BRANCHED HIGHER OLEFIN OLIGOMERIZATION WITH SURFACE MODIFIED ZEOLITE CATALYST

(75) Inventors: Jane C. Cheng, Bridgewater, NJ (US); Sal Miseo, Pittstown, NJ (US); Stuart L. Soled, Pittstown, NJ (US); John S. Buchanan, Lambertville, NJ (US); Jennifer S. Feeley, Lebanon, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 486 days.

(21) Appl. No.: 11/973,101

(22) Filed: Oct. 5, 2007

(65) Prior Publication Data

US 2009/0093663 A1    Apr. 9, 2009

(51) Int. Cl.
  *C07C 2/12* (2006.01)
(52) U.S. Cl. .................. 585/533; 585/510; 585/514; 585/520; 585/527; 585/532
(58) Field of Classification Search .................. None
  See application file for complete search history.

(56) References Cited

U.S. PATENT DOCUMENTS

| | | | |
|---|---|---|---|
| 3,960,978 A | 6/1976 | Givens et al. | |
| 4,021,502 A | 5/1977 | Plank et al. | |
| 4,150,062 A | 4/1979 | Garwood et al. | |
| 4,211,640 A | 7/1980 | Garwood et al. | |
| 4,227,992 A | 10/1980 | Garwood et al. | |
| 4,485,185 A * | 11/1984 | Onodera et al. ............... 502/71 |
| 4,547,613 A | 10/1985 | Garwood et al. | |
| 4,879,038 A | 11/1989 | Namikoshi et al. | |
| 5,026,933 A | 6/1991 | Blain et al. | |
| 2004/0065582 A1 | 4/2004 | Genetti et al. | |
| 2004/0065588 A1 | 4/2004 | Genetti et al. | |
| 2004/0067843 A1 | 4/2004 | Bishop et al. | |
| 2004/0129604 A1 | 7/2004 | Genetti et al. | |

FOREIGN PATENT DOCUMENTS

| | | |
|---|---|---|
| CN | 1316485 | 10/2001 |
| EP | 0 311 310 B1 | 5/1992 |
| SU | 1278348 A1 | 12/1986 |
| SU | 1050246 A1 | 7/1991 |
| WO | WO 2004/033594 A1 | 4/2004 |
| WO | WO 2004/033595 A1 | 4/2004 |

OTHER PUBLICATIONS

R. M. Platz et al., "Catalytic Polymerization of Diesel Fuel" Abstract Attached.

(Continued)

*Primary Examiner*—In Suk Bullock
(74) *Attorney, Agent, or Firm*—Robert A. Migliorini

(57) ABSTRACT

A substantially surface-deactivated catalyst composition that is stable at least to 300° C. The catalyst includes a zeolite catalyst (e.g., ZSM-22, ZSM-23, or ZSM-57) having active internal Brönsted acid sites and a surface-deactivating amount of a rare earth or yttrium oxide (e.g., chosen from lanthanum oxide or lanthanides oxide). This catalyst is preferably used in a process for producing a higher olefin by oligomerizing a light olefin, wherein the process includes contacting a light olefin under oligomerization conditions with the substantially surface-deactivated catalyst composition.

12 Claims, 1 Drawing Sheet

Performance of Yttria-containing ZSM-22

| 200°C | | | | | | | |
|---|---|---|---|---|---|---|---|
| WHSV | Conv | C₈ | C₁₂ | C₁₆ | Me/C₈ | Me/C₁₂ | Me/C₁₆ |
| 0.18 | 86% | 62% | 20% | 10% | 1.19 | 1.71 | 2.14 |

| 200°C | | | | | | | |
|---|---|---|---|---|---|---|---|
| WHSV | Conv | C₈ | C₁₂ | C₁₆ | Me/C₈ | Me/C₁₂ | Me/C₁₆ |
| 0.18 | 88% | 61% | 21% | 10% | 1.26 | 1.77 | 2.16 |

| 200°C | | | | | | | |
|---|---|---|---|---|---|---|---|
| WHSV | Conv | C₈ | C₁₂ | C₁₆ | Me/C₈ | Me/C₁₂ | Me/C₁₆ |
| 0.20 | 92% | 54% | 25% | 12% | 1.37 | 1.94 | 2.17 |

| 250°C | | | | | | | |
|---|---|---|---|---|---|---|---|
| WHSV | Conv | C₈ | C₁₂ | C₁₆ | Me/C₈ | Me/C₁₂ | Me/C₁₆ |
| 1.37 | 87% | 63% | 20% | 8% | 1.25 | 1.83 | 2.14 |

| 300°C | | | | | | | |
|---|---|---|---|---|---|---|---|
| WHSV | Conv | C₈ | C₁₂ | C₁₆ | Me/C₈ | Me/C₁₂ | Me/C₁₆ |
| 10.0 | 72% | 66% | 19% | 6% | 1.24 | 1.87 | 2.07 |

OTHER PUBLICATIONS

G.N. Amezhnova et al., "Effect of Rare Earth Cations on Activity of Y Zeolites in Ethylene Conversions"—Abstract Attached.

O. I., Kuznetsov et al., "Oligomerization of Isobutylene on Zeolite Catalysts"—Abstract Attached.

* cited by examiner

Figure 1

Performance of Yttria-containing ZSM-22

200°C

| WHSV | Conv | $C_8$ | $C_{12}$ | $C_{16}$ | Me/$C_8$ | Me/$C_{12}$ | Me/$C_{16}$ |
|---|---|---|---|---|---|---|---|
| 0.18 | 86% | 62% | 20% | 10% | 1.19 | 1.71 | 2.14 |

200°C

| WHSV | Conv | $C_8$ | $C_{12}$ | $C_{16}$ | Me/$C_8$ | Me/$C_{12}$ | Me/$C_{16}$ |
|---|---|---|---|---|---|---|---|
| 0.18 | 88% | 61% | 21% | 10% | 1.26 | 1.77 | 2.16 |

200°C

| WHSV | Conv | $C_8$ | $C_{12}$ | $C_{16}$ | Me/$C_8$ | Me/$C_{12}$ | Me/$C_{16}$ |
|---|---|---|---|---|---|---|---|
| 0.20 | 92% | 54% | 25% | 12% | 1.37 | 1.94 | 2.17 |

250°C

| WHSV | Conv | $C_8$ | $C_{12}$ | $C_{16}$ | Me/$C_8$ | Me/$C_{12}$ | Me/$C_{16}$ |
|---|---|---|---|---|---|---|---|
| 1.37 | 87% | 63% | 20% | 8% | 1.25 | 1.83 | 2.14 |

300°C

| WHSV | Conv | $C_8$ | $C_{12}$ | $C_{16}$ | Me/$C_8$ | Me/$C_{12}$ | Me/$C_{16}$ |
|---|---|---|---|---|---|---|---|
| 10.0 | 72% | 66% | 19% | 6% | 1.24 | 1.87 | 2.07 |

LIGHTLY BRANCHED HIGHER OLEFIN OLIGOMERIZATION WITH SURFACE MODIFIED ZEOLITE CATALYST

FIELD

The present disclosure generally relates to catalyst compositions for the production of olefin derivatives, for example, higher olefins, wherein the catalyst composition is a 10-ring zeolite whose surface acidity has been modified by incipient wetness treatment with an yttrium or rare earth oxide. The present disclosure is useful in higher olefin production processes using the compositions. This disclosure is useful in processes for higher olefin production with reduced branching of the higher olefins. The catalyst compositions typically comprise 10-ring zeolites with alumina binder and high temperature stable modifiers that reduce the surface acidity.

BACKGROUND

Solid acid catalysts have been used commercially for oligomerization of olefinic feedstock. In an oligomerization process monomers are converted to a finite degree of polymerization. In processes using olefinic feedstock, light olefins ($C_3^=$ to $C_5^=$) are converted typically into branched olefins in the $C_6$-$C_{15}$ range using solid phosphoric acid catalyst (sPa). The sPa process was developed by UOP in the 1930's. This process has a number of drawbacks: (1) low catalyst life due to pellet disintegration causing reactor pressure drop; (2) environmental waste handling problems; and (3) operational and quality constraints limit flexible feedstock. Previously it has been found that acidic zeolites with 10-ring pores, such as ZSM-22, ZSM-23, and ZSM-57, are good alternative catalysts for olefin oligomerization, wherein branched higher olefins are produced from light olefins. These branched higher olefins are further derivatized to branched (OXO) alcohols which in turn are esterified to produce esters that are used as plasticizers. Additionally, these branched higher olefins are hydrogenated to produce desired hydrocarbon solvents. Further, these lightly branched higher olefins are useful in alkylation of benzene or phenol to produce sulfonate detergent precursors. Zeolite technology offers several advantages compared with the older sPa technology including ease of handling, higher catalytic activity, improved product selectivity, and facile catalyst regeneration capability.

U.S. Pat. No. 5,026,933 (Blain et al.) discloses the use of 10-member ring zeolites for higher olefin production. That is, heavy distillate and lubricant range hydrocarbons can be synthesized over ZSM-5 type catalysts at elevated temperature and pressure to provide a product having substantially linear molecular conformations due to the ellipsoidal shape of these catalysts. Conversion of olefins to gasoline and/or distillate products is disclosed in U.S. Pat. Nos. 3,960,978 and 4,021,502 (Givens, Plank and Rosinski) wherein gaseous olefins in the range of ethylene to pentene, either alone or in admixture with paraffins are converted into an olefinic gasoline blending stock by contacting the olefins with a catalyst bed made up of a ZSM-5 type zeolite. Such a technique has been developed by Garwood, et al, as disclosed in European Patent Application No. 83301391.5, published 29 Sep. 1983. In U.S. Pat. Nos. 4,150,062; 4,211,640; 4,227,992; and 4,547,613 Garwood, et al. disclose operating conditions for a process for selective conversion of $C_3$+ olefins to mainly aliphatic hydrocarbons. In the process for catalytic conversion of olefins to heavier hydrocarbons by catalytic oligomerization using a medium pore shape selective acid crystalline zeolite, process conditions can be varied to favor the formation of hydrocarbons of varying molecular weight. At moderate temperature and relatively high pressure, the conversion conditions favor $C_{10}$+ aliphatic product. Lower olefinic feedstocks containing $C_2$-$C_8$ alkenes may be converted; however, the distillate mode conditions do not convert a major fraction of ethylene. A typical reactive feedstock consists essentially of $C_3$-$C_6$ mono-olefins, with varying amounts of non-reactive paraffins and the like being acceptable components. One conventional process for producing substantially linear hydrocarbons by oligomerizing a lower olefin at elevated temperature and pressure comprises contacting the lower olefin under polymerization conditions with siliceous acidic ZSM-23 zeolite having Bronsted acid activity; wherein the zeolite has acidic pore activity and wherein the zeolite surface is rendered substantially inactive for acidic reactions, the zeolite surface being neutralized by a bulky trialkyl pyridine compound having an effective cross-section larger than the zeolite pore.

Although higher olefins produced from zeolite-based catalysts have lower branching than those made with sPa, it is highly desirable to further reduce branching of higher olefin product streams. It is known that collidine (2,4,6-trimethyl pyridine) is an effective agent to deactivate surface acid sites of 10-ring zeolites, thus improving catalyst selectivity toward production of less-branched higher olefin products from olefin containing feedstocks. However, a drawback of collidine is its tendency to desorb from the surface under reaction olefin oligomerization conditions. Desorption is especially troublesome if the oligomerization reaction temperature is higher than 240° C. For olefin oligomerization process, typical commercial end of cycle temperature is about 250° C.

Collidine co-boils with 1-decene and desorbed collidine could contaminate higher olefin products and derivatives, such as branched alcohols produced in a down-stream OXO process. In order to maintain a constant level of collidine on zeolite, a continuous co-feeding of collidine with feed olefin is required. Another drawback of organic-based surface treatment is collindines inability to survive air-regeneration of the spent catalyst. That is, air regeneration burns off the organics, such as collidine. The inorganic species (such as zeolites, yttria and La-oxide) remain intact.

Accordingly, the composition of surface modified 10-ring zeolite catalysts requires the control of the surface acidity of the catalyst to enable a product higher olefin containing stream with low branching levels per molecule. For example, one such technique is to treat the 10-ring zeolite catalyst with an organic base such as collidine. However, because the collidine modified zeolite catalyst is not thermally stable at end of run temperatures, there is leaching of collidine and potentially contamination of the higher olefin containing product stream. Moreover, the high temperature air regeneration of collidine modified catalyst leads to decomposition of the collidine. Therefore, collidine treatment has to be repeated after each air regeneration before the catalyst can be used for higher olefin production.

There is a continuing need for improvement in the catalyst for olefin oligomerization reactions of the type described above. In particular there is a need for effective surface modified zeolite catalysts such that they are stable to end of run olefin oligomerization temperature, do not leach an organic base into the higher olefin product stream and are air regenerable.

The present disclosure provides a novel alternate catalyst system for olefin oligomerization to lightly branched higher olefins, stable to end of oligomerization reaction temperatures, stable to air regeneration, and does not leach organic base to contaminate the higher olefin product stream.

SUMMARY

A substantially surface-deactivated catalyst composition comprising a zeolite catalyst having active internal Brönsted acid sites and containing a surface-deactivating amount of a rare earth or yttrium oxide. Preferably, the catalyst composition is stable at least to about 300° C. (i.e., air regeneration temperature is generally between about 400 to about 540° C.). The catalyst composition preferably exhibits a substantially deactivated surface acidity.

A process for producing a higher olefin by oligomerizing a lower olefin, the process comprising: contacting the lower olefin under oligomerization conditions with a substantially surface-deactivated catalyst composition comprising a zeolite catalyst having active internal Brönsted acid sites and substantially inactive surface acid sites achieved by the presence of a rare earth or yttrium oxide on the surface.

A method of making a higher olefin from a lower olefin containing stream, the method comprising: contacting the olefin containing stream with a surface-deactivited catalyst composition comprising a zeolite catalyst having active internal Brönsted acid sites and substantially inactive surface acid sites achieved by the presence of a rare earth or yttrium oxide on the surface, thereby producing a higher olefin stream and a lighter olefin or vent stream; separating the lighter olefin or vent stream from the higher olefin stream; and contacting a portion of the separated lighter or vent stream with the surface-deactivated catalyst composition. The method further comprising contacting at least a portion of the higher olefin stream with a catalyst for hydroformylation.

These and other features and attributes of the disclosed compositions and oligomerization processes of the present disclosure and their advantageous applications and/or uses will be apparent from the detailed description which follows.

BRIEF DESCRIPTION OF THE DRAWINGS

FIG. 1 depicts the performance of Yttria-containing ZSM-22 according to the present disclosure.

DETAILED DESCRIPTION

A method for the preparation of olefin oligomerization catalysts comprising a ten-ring zeolite with its surface acid sites deactivated with yttrium or a rare earth oxide. Catalyst compositions are disclosed herein. Processes disclosed herein include processes for the oligomerization of light olefin containing feeds comprising contacting one or more olefins with the disclosed catalyst and the subsequent hydroformylation or hydrogenation of the higher olefin to produce alcohols or saturated hydrocarbons. All numerical values within the detailed description and the claims herein are understood as modified by "about."

In step one of an improved oligomerization catalyst preparation, a 10-ring zeolite is treated with an yttrium or rare earth salt solution followed by air calcinations to convert at least some of the surface acid sites to yttrium or rare earth oxide bound sites.

The disclosure describes a method for the preparation of a yttrium or rare earth surface modified 10-ring zeolite oligomerization catalyst system. It describes a process where in step (1) a desired amount of the yttrium or rare earth is reacted as the yttrium or rare earth salt solution with the 10-ring zeolite to reduce the surface acidity of the 10-ring zeolite. Incipient wetness is defined as the condition when just enough liquid has been added to a porous solid to just fill all the pore. If more liquid is added to the mixture, it coats the outer surface, changing the appearance from dull to glistening. On drying, catalyst materials added in an incipient wetness impregnation will deposit in the pores rather than on the outer surface (see "Petroleum Catalysis in Nontechnical Language", by John Magee and Geoffrey Dolbear; copyright 1998 by Pennwell Publishing Company, Tulsa, Okla.

Yttrium oxide and lanthanum oxide are exemplary embodiments of the specific oxides that are useful in this disclosure.

In the second step of the preparative method of the disclosure, the yttria or rare earth bound material formed in step (1) is air dried at 100° C., calcined in air at 400° C. to form corresponding oxide, then cooled and available for use as an oligomerization catalyst.

One of the advantages of this preparative method is that there is an optimum amount of yttrium oxide or rare earth oxide that is reacted with the 10-ring zeolite surface acid sites such that the most desirable product selectivity and reactivity is achieved. Thus, one can control the amount of yttrium or rare earth reagent required. Another advantage of the method disclosed is that the catalyst compositions of this preparative method are thermally stable at temperatures at least to about 300° C., temperatures well above the end or run temperature for olefin oligomerization to higher olefin products. Another advantage of the method disclosed is that the resulting catalyst is useful with both propylene and butene feed streams to generate higher olefin products.

The present disclosure also provides for a process for producing a higher olefin by oligomerizing a lower olefin, the process comprising: contacting the lower olefin under oligomerization conditions with a substantially surface-deactivated catalyst composition comprising a zeolite catalyst having active internal Brönsted acid sites and substantially inactive surface acid sites achieved by the presence of a rare earth or yttrium oxide on the surface.

Additionally, the present disclosure includes a method of making a higher olefin from a lower olefin containing stream, the method comprising: contacting the olefin containing stream with a surface-deactivited catalyst composition comprising a zeolite catalyst having active internal Brönsted acid sites and substantially inactive surface acid sites achieved by the presence of a rare earth or yttrium oxide on the surface, thereby producing a higher olefin stream and a lighter olefin or vent stream; separating the lighter olefin or vent stream from the higher olefin stream; and contacting a portion of the separated lighter or vent stream with the surface-deactivated catalyst composition. The method further comprising contacting at least a portion of the higher olefin stream with a catalyst for hydroformylation.

The method of making a substantially surface-deactivated catalyst composition optionally includes: contacting a zeolite catalyst with a rare earth or yttrium salt solution, followed by air calcination to convert the surface species into the corresponding oxide, and therefore rendering the surface of the zeolite catalyst substantially inactive for acidic reaction. Rare earth or yttrium oxides are solids and cannot be introduced as such. Accordingly, they are introduced as soluble salt solutions (incipient wetness method), then converted to oxides.

This catalyst composition is useful for the preparation of olefin derivatives via olefin oligomerization to produce lightly branched higher olefins. Such lightly branched higher olefins are formed by the method comprising the steps of: (1) treating a zeolite (e.g., a 10-ring zeolite) via incipient wetness with a yttrium or rare earth salt solution, (2) drying the impregnated zeolite catalyst overnight in air at temperature in the range between about 100 to 120° C., preferably 100° C., and (3) heating the impregnated zeolite catalyst in the range between about 350 to 450° C., preferably 400° C., in air for four hours so the yttrium or rare earth is converted to the corresponding oxide, and cooling the catalyst.

The zeolite is chosen from ZSM-22, ZSM-23, or ZSM-57.

The rare earth oxide used to modify the zeolite surface acid sites is chosen from lanthanum oxide or lanthanide oxides.

Furthermore, the present disclosure includes a method for the preparation of lightly branched higher olefins (e.g., between about $C_6$ to about $C_{15}$ range) via olefin oligomerization comprises contacting a $C_3^=$ to $C_5^=$ light olefin containing stream using a modified 10-ring zeolite catalyst where the surface acid sites are at least partly neutralized with yttrium or rare earth oxides.

The reaction of the yttrium or rare earth modified 10-ring zeolite catalyst with the olefin containing stream is conducted at a temperature in the range between about 150 to about 250° C. The reaction of the olefin containing stream with the catalyst is carried at a pressure between about 300 to about 1000 psig and a feed flow rate between about 0.1 to about 10 WHSV.

The olefin in the olefin containing stream is chosen from propylene, butenes including 1- and 2-butene (cis and trans), isobutylene, or pentenes including 1- and 2-pentene (cis and trans), 2-methyl-2-butene or 3-methyl-1-butene.

Sources of the olefin in the olefin containing stream are from a steam cracker stream or from a $C_4^+$ fraction separated from the hydrocarbon product produced by an oxygenate to olefin reaction unit. $C_4$ hydrocarbon mixtures are generally available in any refinery employing steam cracking to produce olefins; a crude steam cracked butene stream, Raffinate-1 (the product of remaining after solvent extraction or hydrogenation to remove butadiene from the crude steam cracked butene stream) and Raffinate-2 (the product remaining after removal of butadiene and isobutene from the crude steam cracked butene stream). Generally, these streams have compositions within the weight ranges indicated in Table A below.

TABLE A

| Component | Crude $C_4$ stream | Raffinate 1 Solvent Extraction | Raffinate 1 Hydrogenation | Raffinate 2 Solvent Extraction | Raffinate 2 Hydrogenation |
|---|---|---|---|---|---|
| Butadiene | 30-85% | 0-2% | 0-2% | 0-1% | 0-1% |
| C4 acetylenes | 0-15% | 0-0.5% | 0-0.5% | 0-0.5% | 0-0.5% |
| Butene-1 | 1-30% | 20-50% | 50-95% | 25-75% | 75-95% |
| Butene-2 | 1-15% | 10-30% | 0-20% | 15-40% | 0-20% |
| Isobutene | 0-30% | 0-55% | 0-35% | 0-5% | 0-5% |
| N-butane | 0-10% | 0-55% | 0-10% | 0-55% | 0-10% |
| Iso-butane | 0-1% | 0-1% | 0-1% | 0-2% | 0-2% |

Other refinery mixed $C_4$ streams, such as those obtained by catalytic cracking of naphthas and other refinery feedstocks, typically have the following composition:

| Propylene | 0-2 wt % |
|---|---|
| Propane | 0-2 wt % |
| Butadiene | 0-5 wt % |
| Butene-1 | 5-20 wt % |
| Butene-2 | 10-50 wt % |
| Isobutene | 5-25 wt % |
| Iso-butane | 10-45 wt % |
| N-butane | 5-25 wt % |

$C_4$ hydrocarbon fractions obtained from the conversion of oxygenates, such as methanol, to lower olefins more typically have the following composition:

| Propylene | 0-1 wt % |
|---|---|
| Propane | 0-0.5 wt % |
| Butadiene | 0-1 wt % |
| Butene-1 | 10-40 wt % |
| Butene-2 | 50-85 wt % |
| Isobutene | 0-10 wt % |
| N-+ iso-butane | 0-10 wt % |

Any one or any mixture of the above $C_4$ hydrocarbon mixtures can be used in the process of the invention. In addition to linear butenes and butanes, these mixtures typically contain components, such as isobutene and butadiene, which can be deleterious to the process of the invention. For example, the normal alkylation products of isobutene with benzene are tert-butylbenzene and iso-butylbenzene which, as previously stated, act as inhibitors to the subsequent oxidation step. Thus, prior to the alkylation step, these mixtures preferably are subjected to butadiene removal and isobutene removal. For example, isobutene can be removed by selective dimerization or reaction with methanol to produce MTBE, whereas butadiene can be removed by extraction or selective hydrogenation to butene-1.

In addition to other hydrocarbon components, commercial $C_4$ hydrocarbon mixtures typically contain other impurities which could be detrimental to the alkylation process. For example, refinery $C_4$ hydrocarbon streams typically contain nitrogen and sulfur impurities, whereas $C_4$ hydrocarbon streams obtained by oxygenate conversion process typically contain unreacted oxygenates and water. Thus, prior to the alkylation step, these mixtures may also be subjected to one or more of sulfur removal, nitrogen removal and oxygenate removal, in addition to butadiene removal and isobutene removal. Removal of sulfur, nitrogen, oxygenate impurities is conveniently effected by one or a combination of caustic treatment, water washing, distillation, adsorption using molecular sieves and/or membrane separation. Water is also typically removed by adsorption.

Although not preferred, it is also possible to employ a mixture of a $C_4$ alkylating agent, as described above, and $C_3$ alkylating agent, such as propylene, as the alkylating agent in the alkylation step of the invention so that the alkylation step produces a mixture of cumene and sec-butylbenzene. The resultant mixture can then be processed through oxidation and cleavage, to make a mixture of acetone and MEK, along with phenol, preferably where the molar ratio of acetone to phenol is 0.5:1, to match the demand of bisphenol-A production.

A still further method of making higher olefins from light olefin containing stream includes contacting the light olefin containing stream with an oligomerization catalyst comprising a yttrium or rare earth modified 10-ring zeolite catalyst composition to produce a product containing higher olefin and a vent stream; separating the vent stream from the higher olefin; and contacting a portion of the separated vent stream with the oligomerization catalyst.

In another embodiment the present disclosure relates to a higher olefin product derived from a $C_4^+$ feed stream, the product characterized by having a low extent of branching.

A higher olefin $C_8$ and $C_{12}$ product composition having a product branching defined as: Branching=0x% linear+1x% mono-branched+2×% di-branched+3×% tri-branched, where: % linear+% mono-branched+% di-branched+% tri-branched=100%.

A higher olefin $C_{16}$ product composition having a product branching defined as: Branching=0×% linear+1×% mono-branched+2.5×% (di- and tri-branched) where: % linear+% mono-branched+% (di- and tri-branched)=100%.

In another embodiment the present disclosure relates to a higher olefin product derived from a propylene containing feed stream, the product characterized by having a low extent of branching.

A higher olefin $C_6$ product composition having a product branching defined as: Branching=0×% linear+1×% mono-branched+2×% di-branched, where: % linear+% mono-branched+% di-branched=100%.

A higher olefin $C_9$ and $C_{12}$ product composition having a product branching defined as: Branching=0×% linear+1×% mono-branched+2×% di-branched+3×% tri-branched, where: % linear+% mono-branched+% di-branched+% tri-branched=100%.

In another embodiment of the disclosure, the olefin derivatives from the catalytic olefin oligomerization process are further converted via hydroformylation and hydrogenation to branched alcohols. The branched alcohols are usefully esterified with, for example, phthalic anhydride, adipic acid, or trimellitic anhydride to generate esters useful as plasticizers.

In another embodiment of the disclosure, the higher olefin products from the catalytic olefin oligomerization process are further converted via hydrogenation to branched saturated hydrocarbons. The branched saturated hydrocarbons are usefully applied as functional fluids. Furthermore, these higher olefins can be further converted via alkylation with benzene or phenol to make sulfonate detergent precursors.

The following examples illustrate the present disclosure and the advantages thereto without limiting the scope thereof.

EXAMPLES

Experimental Details:

Below are examples of the preparation of comparative catalysts using collidine as the surface modifying agent (Comparative Example 1) and of the catalyst systems of this disclosure. Other species within the range of the detailed description of the disclosure may work.

Comparative Example 1

Preparation of Collidine/ZSM-22

The ZSM-22 catalyst is a ⅛" trilobe extrudate with 75% zeolite and 25% alumina binder. This zeolite crystal has a $SiO_2/Al_2O_3$ molar ratio of 65. This is the base case catalyst used for surface modification. See U.S. Pat. Nos. 4,481,177, 4,556,477, and 4,902,406 assigned to Mobil Chemical Company, which are incorporated herein in their entirety by reference thereto.

8.5 g of ZSM-22 as ⅛" trilobe extrudates as defined above was used for collidine treatment. 20 cc of pentane were added to a round-bottom flask containing the catalyst. 10 cc of pentane were added to a jar containing 0.077 g of collidine (2,4,6-Trimethylpyridine, 99% purity from Aldrich, CAS #108-75-8). The collidine solution was added to the flask. The final mixture was allowed to stand at room temperature for two hours with occasional shaking. Pentane was removed by purging the flask with nitrogen. The catalyst was dried to a constant weight at room temperature under vacuum. The resulting catalyst had a collidine/Al (zeolitic Al) molar ratio of 0.2.

Example 2

Preparation of Yttria/ZSM-22

The same base case ZSM-22 catalyst as described in Comparative Example 1 was used for preparation of a yttria-containing catalyst. 0.287 g of yttrium nitrate hexahydrate ($Y(NO_3)_3 6H_2O$ from Aldrich, CAS #13494-98-9) was dissolved in water to make a solution with a volume of 7 cc and this solution was impregnated by incipient wetness onto 10 grams of ⅛" trilobe extrudates of alumina-bound ZSM-22. The sample was dried in air at 100° C. overnight and heated in air at 0.5° C./min to 400° C., held at that temperature for 4 hours, and then cooled to room temperature. The finished catalyst, designated as 24151-163 below, contains 0.84 wt % of yttria and has a Y/Al (zeolitic Al) molar ratio of 0.2. The amounts of materials used for this preparation are shown in Table 1.

Additional catalyst samples containing different levels of yttria on ZSM-22 were prepared using the same procedure described above by adjusting the amount of yttrium nitrate impregnated onto the extrudates. Wettability was maintained at 0.70 cc solution per gram of catalyst. Drying and calcination conditions were the same as with sample 24151-163. The amounts of materials used for preparation are also shown in Table 1.

TABLE 1

Variation of Y2O3 Loading on ZSM-22

| Sample # | Weight of Yttrium Nitrate, g | Weight of ZSM-22 Extrudates, g | Wt % of $Y_2O_3$ on ZSM-22 | Y/Al Molar Ratio (zeolitic Al) |
|---|---|---|---|---|
| 24151-162 | 0.143 | 10 | 0.42 | 0.1 |
| 24151-163 | 0.287 | 10 | 0.84 | 0.2 |
| 24151-173 | 1.160 | 20 | 1.68 | 0.4 |
| 24151-193 | 1.750 | 20 | 2.52 | 0.6 |

Example 3

Preparation of Lanthanum Oxide/ZSM-22

Samples similar to those described in Example 2 were prepared but with lanthanum oxide rather than yttrium oxide impregnated onto ZSM-22 extrudates. The two compositions shown in Table 2 were prepared in an analogous way to those shown in Example 2 using lanthanum nitrate hexahydrate ($La(NO_3)_3.6H_2O$ from Aldrich, CAS #10277-43-77) as the lanthanum source and with wettabilities at 0.70 cc/g catalyst. Drying and calcination conditions were the same as shown in Example 2.

TABLE 2

Lanthanum Oxide on ZSM-22

| Sample | Sample # | Weight of Lanthanum Nitrate, g | Weight of ZSM-22 Extrudates, g | Y/Al Ratio (Zeolitic Al) |
|---|---|---|---|---|
| 1.22 wt % $La_2O_3$ | 24151-173-A | 0.65 | 20 | 0.2 |
| 2.44 wt % $La_2O_3$ | 24151-193-A | 1.33 | 20 | 0.4 |

Below are examples of the oligomerization process using the catalysts prepared in Comparative Example 1, Example 2, and Example 3 above. Other species within the range of the detailed description of the disclosure may work.

Example 4

2-Butene Oligomerization with Untreated ZSM-22

Two grams of base case ZSM-22, as ⅛" trilobe extrudate with 25% alumina binder, was used for oligomerization. The catalyst was diluted with sand to 18 cc and charged to an isothermal, down-flow, 0.5" inch (inside diameter) fixed-bed reactor. The catalyst was dried at 150° C. and atmospheric pressure with 100 cc/min flowing $N_2$ for 2 hours. $N_2$ was turned off and the reactor pressure was set to 750 psig by a grove loader. The 2-butene feed (57.1% cis-butene, 37.8% trans-butene, 2.5% n-butane, 0.8% isobutene and 1-butene, 1.8% others) was introduced into the reactor at 60 cc/hr for 2 hour, then reduced to 1.7 WHSV while the reactor pressure was increased to 750 psig. After reaching 750 psig, the reactor temperature was ramped at 2° C./min to 200° C. After line out for 12 hours at 200° C., 750 psig, and 1.7 WHSV on 2-butene feed, liquid products were collected in a cold trap. Additional samples were collected at 2.2 WHSV on 2-butene feed. Representative data are shown in Table 3.

Product carbon number distribution was determined with an HP-5890 GC equipped with a 60 meter DB-1 column (0.25 mm id and 1 μm film thickness). Product branching was determined with an $H_2$-GC. This was an HP-5890 GC equipped with (a) a 100 meter DB-1 column (0.25 mm id and 0.5 μm film thickness); (b) hydrogen as the carrier gas; and (c) 0.1 g of 0.5% Pt/alumina catalyst in the GC insert for in-situ hydrogenation. Both GC used the same temperature program: 2 min at −20° C., 8° C./min to 275° C., hold at 275° C. for 35 min. Branching values were determined by the following formulas:

For $C_8$ and $C_{12}$ olefins:

Branching=0×% linear+1×% mono-branched+2×% di-branched+3×% tri-branched

Where: % linear+% mono-branched+% di-branched+% tri-branched=100%

For $C_{16}$ olefins:

Branching=0×% linear+1×% mono-branched+2.5×% (di- and tri-branched)

Where: % linear+% mono-branched+% (di- and tri-branched)=100%

An average branching index of 2.5 was used for di- and tri-branched $C_{16}$ species since these components overlapped on our $H_2$-GC. Representative data are tabulated below.

Comparative Example 5

2-Butene Oligomerization with Collidine/ZSM-22

Eight grams of collidine-treated ZSM-22, as prepared in Comparative Example 1, was used for oligomerization. The catalyst was diluted with sand to 18 cc and charged to an isothermal, down-flow, 0.5 inch (inside diameter) fixed-bed reactor. The catalyst was dried at 150° C. and atmospheric pressure with 100 cc/min flowing $N_2$ for 2 hours. $N_2$ was turned off and reactor pressure was set to 750 psig by a grove loader. The 2-butene feed (57.1% cis-butene, 37.8% trans-butene, 2.5% n-butane, 0.8% isobutene and 1-butene, 1.8% others) was introduced into the reactor at 60 cc/hr for 2 hours, then reduced to 0.18 WHSV (2.3 cc/hr) while the reactor pressure was increased to 750 psig. After reaching 750 psig, the reactor temperature was ramped at 2° C./min to 200° C. After line out for 12 hours at 200° C., 750 psig, and 0.18 WHSV on 2-butene feed, liquid products were collected in a cold trap. Representative data are shown in Table 3.

Data in Table 3 show that collidine-treated ZSM-22 is effective for reducing branching of olefin products while maintaining octene selectivity. The loss of catalyst activity after surface treatment, as reflected by the reduced feed flow rate to achieve constant conversion, indicates that surface acid sites were titrated by collidine.

However, when the catalyst was tested at elevated temperatures (up to 260° C.), a loss of collidine was observed. The loss was evident at 260° C., which resulted in an increase in catalyst activity and product branching. Representative data are shown in Table 4b.

TABLE 3

2-Butene Oligomerization with ZSM-22 and Collidine-Treated ZSM-22

| Catalyst | ZSM-22 Untreated | ZSM-22 with Collidine |
|---|---|---|
| Base/Al Molar Ratio | — | 0.2 collidine/Al |
| Sample Identification | 508A096005 | 508A087005 |
| Temperature, ° C. | 199 | 200 |
| Pressure, psig | 760 | 747 |
| Feed Flow Rate, WHSV | 2.2 | 0.25 |
| Days on Stream | 6.7 | 4.8 |
| Conversion % | 57.6 | 54.7 |
| Selectivity, wt % | | |
| C4− | 0.00 | 0.00 |
| C5-7 | 0.48 | 0.54 |
| C8= | 75.74 | 76.80 |
| C9-11 | 0.22 | 0.21 |
| C12= | 15.40 | 20.27 |
| C16= | 5.84 | 1.84 |
| C20= | 1.91 | 0.27 |
| C24+ | 0.40 | 0.08 |
| Sum | 100.0 | 100.0 |
| Product Branching | | |
| Me/C8 | 1.41 | 0.97 |
| Me/C12 | 2.05 | 1.13 |
| Me/C16 | 2.28 | 1.77 |

Example 6

2-Butene Oligomerization with Yttria/ZSM-22

Eight grams of ZSM-22, containing 1.68 wt % of yttria (Sample #24151-173) as prepared in Example 2, was used for oligomerization. The same procedure described in Example 5 was used to start up the run. The catalyst was tested under a variety of process conditions as shown in FIG. 1 (arrows indicate sequence of conditions for data collection). After testing at 250° C. and 300° C., the catalyst performance was re-evaluated at startup conditions (200° C., 0.18-0.2 WHSV or SV), respectively (FIG. 1).

Representative data are compared with that of untreated ZSM-22 in Table 4a. The data show that yttria-containing ZSM-22 is effective for reducing branching of olefin products while maintaining octene selectivity. The loss of catalyst activity after surface treatment, as reflected by the reduced feed flow rate to achieve constant conversion, indicates that at least some of the surface acid sites were titrated by yttria. The data also show that yttria-containing ZSM-22 can be operated at 200-300° C. to produce higher olefins with reduced branching.

TABLE 4a

2-Butene Oligomerization with ZSM-22 and Yttria-Treated ZSM-22

| | Catalyst | | | | |
|---|---|---|---|---|---|
| | ZSM-22 untreated | ZSM-22 with collidine | ZSM-22 with 1.68 wt % $Y_2O_3$ | | |
| Base/Al Molar Ratio | — | 0.2 collidine/Al | 0.4 Y/Al | 0.4 Y/Al | 0.4 Y/Al |
| Run Identification | 508A096005 | 508A087014 | 508B091005 | 508B091011 | 508B091019 |
| Temperature, ° C. | 199 | 200 | 200 | 250 | 300 |
| Pressure, psig | 760 | 738 | 747 | 759 | 753 |
| Feed Flow Rate, WHSV | 2.2 | 0.18 | 0.18 | 1.4 | 10.0 |
| Days on Stream | 6.7 | 15.8 | 4.8 | 16.3 | 23.9 |
| Conversion % | 57.6 | 65.2 | 66.3 | 86.7 | 72.3 |
| Selectivity, wt % | | | | | |
| C4– | 0.00 | 0.01 | 1.27 | 4.96 | 3.59 |
| C5-7 | 0.48 | 0.61 | 0.54 | 1.11 | 2.57 |
| C8= | 75.74 | 71.76 | 69.50 | 63.60 | 66.27 |
| C9-11 | 0.22 | 0.23 | 0.21 | 0.71 | 1.39 |
| C12= | 15.40 | 23.44 | 16.97 | 19.39 | 19.31 |
| C16= | 5.84 | 2.93 | 8.23 | 7.88 | 5.73 |
| C20= | 1.91 | 0.94 | 3.22 | 2.30 | 1.10 |
| C24+ | 0.40 | 0.08 | 0.06 | 0.04 | 0.00 |
| Sum | 100.0 | 100.00 | 100.0 | 100.0 | 100.0 |
| Product Branching | | | | | |
| Me/C8 | 1.41 | 1.02 | 1.14 | 1.24 | 1.24 |
| Me/C12 | 2.05 | 1.22 | 1.76 | 1.79 | 1.87 |
| Me/C16 | 2.28 | 1.89 | 2.25 | 2.08 | 2.07 |

Representative data of yttria/ZSM-22 are also compared with that of collidine/ZSM-22 in Table 4b. After a high temperature data collection (260° C. with collidine/ZSM-22 and 300° C. with yttria/ZSM-22), C8 branching (Me/C8) for both catalysts experienced an increase. However, the branching increase for yttria/ZSM-22 catalyst with a delta temperature of 100° C. is comparable with that of collidine/ZSM-22 with a delta temperature of 60° C., indicating the more stable nature of yttira/ZSM-22 to elevated temperatures.

TABLE 4b

2-Butene Oligomerization with Collidine/ZSM-22 and Yttria/ZSM-22

| | Catalyst | | | | | |
|---|---|---|---|---|---|---|
| | Collidine/ZSM-22 | | | 1.68 wt % $Y_2O_3$/ZSM-22 | | |
| Base/Al Molar Ratio | 0.2 Collidine/Al | | | 0.4 Y/Al | | |
| Run Identification | 508A087014 | 508A087022 | 508A087024 | 508B091005 | 508B091019 | 508B091023 |
| Temperature, ° C. | 200 | 260 | 200 | 200 | 300 | 200 |
| Pressure, psig | 738 | 755 | 746 | 747 | 753 | 751 |
| Feed Flow Rate, WHSV | 0.18 | 3.1 | 0.19 | 0.18 | 10.0 | 0.19 |
| Days on Stream | 15.8 | 20.2 | 23.8 | 4.8 | 23.9 | 26.8 |
| Conversion % | 65.2 | 78.3 | 86.1 | 66.3 | 72.3 | 91.4 |
| Selectivity, wt % | | | | | | |
| C4– | 0.01 | 1.21 | 0.00 | 1.27 | 3.59 | 2.81 |
| C5-7 | 0.61 | 1.39 | 0.60 | 0.54 | 2.57 | 0.64 |
| C8= | 71.76 | 63.68 | 59.68 | 69.50 | 66.27 | 52.04 |
| C9-11 | 0.23 | 0.85 | 0.30 | 0.21 | 1.39 | 0.48 |
| C12= | 23.44 | 25.46 | 30.79 | 16.97 | 19.31 | 26.40 |
| C16= | 2.93 | 5.28 | 5.89 | 8.23 | 5.73 | 12.82 |
| C20= | 0.94 | 1.60 | 2.34 | 3.22 | 1.10 | 4.70 |
| C24+ | 0.08 | 0.52 | 0.41 | 0.06 | 0.00 | 0.10 |
| Sum | 100.0 | 100.0 | 100.0 | 100.0 | 100.0 | 100.0 |
| Product Branching | | | | | | |
| Me/C8 | 1.02 | 1.15 | 1.19 | 1.14 | 1.24 | 1.29 |
| Me/C12 | 1.22 | 1.48 | 1.43 | 1.76 | 1.87 | 1.96 |
| Me/C16 | 1.89 | 1.97 | 2.05 | 2.25 | 2.07 | 2.15 |

Catalysts with 0.42, 0.84 and 2.52 wt % yttria, as prepared in Example 2, were also tested for 2-butene oligomerization. It was found that the 0.42% and 0.84% yttria samples did not have sufficient levels of yttria on catalysts surface to reduce product branching. The 2.52% yttria sample, on the other hand, had a little too much yttria on the catalyst. The excess yttria did not perform as well as the 1.68 wt % yttria sample.

Example 7

2-Butene Oligomerization with Lanthanum Oxide/ZSM-22

Eight grams of ZSM-22, containing 2.44 wt % of $La_2O_3$ as prepared in Example 3, was used for oligomerization. The same procedure described in Example 5 was used to start up the run. The catalyst was tested at 200° C. Representative data are compared with that of ZSM-22, collidine-treated ZSM-22, yttria-treated ZSM-22 in Table 5. The data show that $La_2O_3$-containing ZSM-22 is effective for reducing branching of olefin products while maintaining octene selectivity. The loss of catalyst activity after surface treatment, as reflected by the reduced feed flow rate to achieve constant conversion, indicates that at least some of the surface acid sites were titrated by $La_2O_3$.

TABLE 5

Comparison of Catalyst Performance for 2-Butene Oligomerization

| Catalyst | ZSM-22 Untreated | ZSM-22 with collidine | ZSM-22 with 1.68% $Y_2O_3$ | ZSM-22 with 2.44% $La_2O_3$ |
|---|---|---|---|---|
| Base/Al Molar Ratio | — | 0.2 collidine/Al | 0.4 Y/Al | 0.4 La/Al |
| Run Identification | 508A096005 | 508A087014 | 508A091004 | 508A098011 |
| Temperature, ° C. | 199 | 200 | 200 | 200 |
| Pressure, psig | 760 | 738 | 725 | 776 |
| Feed Flow Rate, WHSV | 2.2 | 0.18 | 0.17 | 0.18 |
| Days on Stream | 6.7 | 15.8 | 3.8 | 20.8 |
| Conversion % | 57.6 | 65.2 | 66.3 | 55.01 |
| Selectivity, wt % | | | | |
| C4- | 0.00 | 0.01 | 0.84 | 0.00 |
| C5-7 | 0.48 | 0.61 | 0.70 | 0.56 |
| C8= | 75.74 | 71.76 | 72.10 | 75.57 |
| C9-11 | 0.22 | 0.23 | 0.27 | 0.48 |
| C12= | 15.40 | 23.44 | 16.74 | 16.18 |
| C16= | 5.84 | 2.93 | 7.47 | 6.22 |
| C20= | 1.91 | 0.94 | 1.85 | 0.99 |
| C24+ | 0.40 | 0.08 | 0.03 | 0.00 |
| Sum | 100.0 | 100.0 | 100.0 | 100.0 |
| Product Branching | | | | |
| Me/C8 | 1.41 | 1.02 | 1.15 | 1.16 |
| Me/C12 | 2.05 | 1.22 | 1.74 | 1.72 |
| Me/C16 | 2.28 | 1.89 | 2.21 | 2.11 |

Example 8

Propylene Oligomerization with ZSM-22

0.5 gram of base case ZSM-22 was used for propylene oligomerization. A similar startup procedure described in Example 5 was used to start the run using propylene feed (99% purity) as feed. The catalyst was tested at 200° C. Representative data are shown in Table 6. Branching values were determined by the following formulas.

For $C_6$ olefins:

Branching=0×% linear+1×% mono-branched+2×% di-branched

Where: % linear+% mono-branched+% di-branched=100%

For $C_9$ and $C_{12}$ olefins:

Branching=0×% linear+1×% mono-branched+2×% di-branched+3×% tri-branched

Where: % linear+% mono-branched+% di-branched+% tri-branched=100%

Example 9

Propylene Oligomerization with Yttria/ZSM-22

1.4 grams of ZSM-22, containing 0.84 wt % of $Y_2O_3$ as prepared in Example 2, were used for propylene oligomerization. A similar startup procedure described in Example 5 was used to start the run using propylene (99% purity) as feed. The catalyst was tested at 200° C. Representative data are shown in Table 6.

Tests were also conducted using ZSM-22 modified with three different levels of yttria, as prepared in Example 2 (0.42 wt % $Y_2O_3$, sample 24151-162; 1.68 wt % $Y_2O_3$, sample 24151-173; and 2.52 wt % $Y_2O_3$, sample 24151-193). The catalyst was tested at 200° C. Representative data are shown in Table 6.

Example 10

Propylene Oligomerization with Lanthanum Oxide/ZSM-22

Tests were also conducted using ZSM-22 modified with two different levels of lanthanum oxide, as prepared in Example 3. A similar startup procedure described in Example 5 was used to start the run using propylene (99% purity) as feed. The 1.22 wt % $La_2O_3$ sample was tested at 200° C. The 2.44 wt % $La_2O_3$ sample was tested at 230° C. due to its reduced activity. Representative data are also shown in Table 6.

The results in Table 6 show that ZSM-22 catalysts modified with yttria or lanthanum oxide are effective for reducing branching of the $C_9$ and $C_{12}$ higher olefin products. The loss of catalyst activity after surface treatment, as reflected by the reduced feed flow rate to achieve similar conversion, indicates that at least some of the surface acid sites were titrated by yttria or lanthanum oxide.

TABLE 6

Comparison of Propylene Oligomerization Data

ZSM-22 Catalyst

|  | Untreated | 0.42 wt % $Y_2O_3$ | 0.84 wt % $Y_2O_3$ | 1.68 wt % $Y_2O_3$ | 2.52 wt % $Y_2O_3$ | 1.22 wt % $La_2O_3$ | 2.44 wt % $La_2O_3$ |
|---|---|---|---|---|---|---|---|
| Y/Al or La/Al Molar Ratio |  | 0.1 | 0.2 | 0.4 | 0.6 | 0.2 | 0.4 |
| Sample # | — | 24151-162 | 24151-163 | 24151-173 | 24151-193 | 24151-173-A | 24151-193-A |
| Run Identification | 512A011-13 | 512A027-2 | 512A022-3 | 512A024-2 | 512A026-1 | 512A025-5 | 512A033-10 |
| Temperature, °C. | 200 | 201 | 200 | 200 | 201 | 200 | 230 |
| Pressure, psig | 760 | 751 | 754 | 748 | 752 | 756 | 753 |
| Feed Flow Rate, WHSV | 8.0 | 2.8 | 1.6 | 1.6 | 1.7 | 1.6 | 13 |
| Days on Stream | 7.9 | 1.8 | 2.8 | 1.8 | 0.8 | 4.8 | 6.8 |
| Conversion % | 91.3 | 82.34 | 87.2 | 88.4 | 71.3 | 81.8 | 92.93 |
| Selectivity, wt % |  |  |  |  |  |  |  |
| C3 | 0.19 | 0.00 | 0.00 | 0.00 | 0.00 | 0.00 | 0.00 |
| C4=s | 0.04 | 0.05 | 0.04 | 0.05 | 0.03 | 0.05 | 0.10 |
| C4 | 0.02 | 0.01 | 0.04 | 0.02 | 0.02 | 0.04 | 0.02 |
| C5s | 1.88 | 0.16 | 0.23 | 0.28 | 0.25 | 0.19 | 0.31 |
| C6 | 46.03 | 62.99 | 58.86 | 51.06 | 60.50 | 62.77 | 56.75 |
| C7-8 | 0.56 | 0.32 | 0.41 | 0.63 | 0.50 | 0.42 | 0.57 |
| C9 | 34.19 | 23.64 | 24.72 | 27.12 | 22.69 | 22.78 | 27.09 |
| C10-11 | 0.57 | 0.23 | 0.29 | 0.62 | 0.22 | 0.31 | 0.47 |
| C12 | 14.90 | 10.72 | 12.71 | 16.13 | 12.73 | 11.34 | 12.03 |
| C15 | 1.27 | 1.47 | 2.25 | 2.92 | 2.53 | 1.75 | 2.11 |
| C16+ | 0.35 | 0.41 | 0.42 | 1.16 | 0.52 | 0.32 | 0.55 |
| Sum | 100.0 | 100.0 | 100.0 | 100.0 | 100.0 | 100.0 | 100.0 |
| Product Branching |  |  |  |  |  |  |  |
| Me/C6 | 0.93 | 0.92 | 0.92 | 0.92 | 0.91 | 0.92 | 0.90 |
| Me/C9 | 1.85 | 1.63 | 1.58 | 1.61 | 1.62 | 1.56 | 1.49 |
| Me/C12 | 2.42 | 2.32 | 2.30 | 2.32 | 2.32 | 2.30 | 2.17 |

The examples above show that rare earth and yttrium oxides can be used to modify surface acid sites of 10-ring zeolites such as ZSM-22. When used for olefin oligomerization, the modified catalysts are effective for reducing product branching. Most importantly, the modified catalyst can be used at 200-300° C. to produce higher olefins. Therefore, these catalysts should survive commercial end of cycle temperature of about 250° C. Unlike collidine which decomposes during air regeneration, rare earth and yttrium oxides are stable and should survive oxidative catalyst regeneration.

Applicants have attempted to disclose all embodiments and applications of the disclosed subject matter that could be reasonably foreseen. However, there may be unforeseeable, insubstantial modifications that remain as equivalents. While the present disclosure has been described in conjunction with specific, exemplary embodiments thereof, it is evident that many alternations, modifications, and variations will be apparent to those skilled in the art in light of the foregoing description without departing from the spirit or scope of the present disclosure. Accordingly, the present disclosure is intended to embrace all such alterations, modifications, and variations of the above detailed description. All patents and other documents cited herein, including priority documents, are fully incorporated by reference to the extent such disclosure is not inconsistent with this disclosure and for all jurisdictions in which such incorporation is permitted. When numerical lower limits and numerical upper limits are listed herein, ranges from any lower limit to any upper limit are contemplated.

What is claimed is:

1. A process for producing a higher olefin by oligomerizing a light olefin, said process comprising: contacting said light olefin under oligomerization conditions with a surface-deactivated catalyst composition comprising a zeolite catalyst having active internal Brönsted acid sites and containing a surface-deactivating amount of a rare earth or yttrium oxide wherein the amount ranges from greater than 0.84 wt % to less than 2.52 wt %.

2. The process according to claim 1, wherein said catalyst composition is stable at least to 300° C.

3. The process according to claim 1, wherein said zeolite catalyst is chosen from ZSM-22, ZSM-23, or ZSM-57.

4. The process according to claim 1, wherein said rare earth oxide is chosen from lanthanum oxide or lanthanides oxide.

5. The process according to claim 1, wherein said zeolite catalyst is a 10-ring zeolite.

6. The process according to claim 1, wherein said higher olefin has a methyl branching in the range between about 0.9 to 2.5.

7. The process according to claim 1, wherein said lower olefin to said higher olefin conversion is in the range between about 45 to 95%.

8. A method of making a higher olefin from a light olefin containing stream, said method comprising:
   contacting the olefin containing stream with a surface-deactivated catalyst composition comprising a zeolite catalyst having active internal Brönsted acid sites and containing a surface-deactivating amount of a rare earth or yttrium oxide, wherein the amount ranges from greater than 0.84 wt % to less than 2.52 wt % thereby producing a higher olefin and a vent stream;

separating said vent stream from said higher olefin; and contacting a portion of said separated vent stream with said surface-deactivated catalyst composition.

9. The method of claim 8, wherein said substantially surface-deactivated catalyst composition is a 10-ring zeolite.

10. The method of claim 9, wherein said 10-ring zeolite is chosen from ZSM-22, ZSM-23, or ZSM-57 catalysts.

11. The method of claim 8, wherein said substantially surface-deactivated catalyst composition is stable at least to 300° C.

12. The method of claim 8 further comprising contacting at least a portion of said higher olefin with a hydroformylation catalyst.

* * * * *